(12) United States Patent
Carmel et al.

(10) Patent No.: US 6,796,982 B2
(45) Date of Patent: Sep. 28, 2004

(54) INSTANT IGNITION ELECTROSURGICAL PROBE AND METHOD FOR ELECTROSURGICAL CUTTING AND ABLATION

(75) Inventors: Yuval Carmel, Rockville, MD (US); Anatoly Shkvarunets, Rockville, MD (US)

(73) Assignee: Electrosurgery Associates, LLC, Rockville, MD (US)

( * ) Notice: Subject to any disclaimer, the term of this patent is extended or adjusted under 35 U.S.C. 154(b) by 239 days.

(21) Appl. No.: 10/157,966

(22) Filed: May 31, 2002

(65) Prior Publication Data

US 2002/0183741 A1 Dec. 5, 2002

Related U.S. Application Data

(60) Provisional application No. 60/295,700, filed on Jun. 5, 2001.

(51) Int. Cl.[7] .............................................. A61B 18/18
(52) U.S. Cl. .............................. 606/41; 606/45; 606/49
(58) Field of Search ............................. 606/41, 45, 47, 606/49

(56) References Cited

U.S. PATENT DOCUMENTS

| | | |
|---|---|---|
| 4,901,719 A | 2/1990 | Trenconsky et al. |
| 5,080,660 A | 1/1992 | Buelna |
| 5,891,095 A | 4/1999 | Eggers et al. |
| 6,066,134 A | 5/2000 | Eggers et al. |
| 6,159,194 A | 12/2000 | Eggers et al. |
| 6,168,594 B1 | 1/2001 | LaFontaine et al. |
| 6,312,408 B1 | 11/2001 | Eggers et al. |
| 6,371,956 B1 | 4/2002 | Wilson et al. |

FOREIGN PATENT DOCUMENTS

| | | |
|---|---|---|
| EP | 1 095 627 A1 | 5/2001 |
| WO | WO 00/62685 | 10/2000 |

*Primary Examiner*—Michael Peffley
*Assistant Examiner*—Aaron Roane
(74) *Attorney, Agent, or Firm*—Dickstein Shapiro Morin & Oshinsky LLP (57) ABSTRACT

An electrosurgical electrode capable of achieving instant ignition in a conductive fluid and a method of conducting an electrosurgical procedure with such electrode are disclosed. The electrosurgical electrode comprises a metallic body portion of various geometries, a metallic tip and a dielectric insulator adjacent the metallic body portion. The metallic tip is recessed from the surface of the dielectric so that the dielectric material and the adjacent recessed metallic tip form a high current density zone and pocket for bubble entrapment and instant spark formation.

20 Claims, 7 Drawing Sheets

INSTANT IGNITION ELECTROSURGICAL PROBE AND METHOD FOR ELECTROSURGICAL CUTTING AND ABLATION

The present application claims the benefit under 35 U.S.C. 119(e) of U.S. Provisional Application Ser. No. 60/295,700 filed on Jun. 5, 2001, the disclosure of which is incorporated by reference herein.

FIELD OF THE INVENTION

The present invention relates to the field of electrosurgery and, in particular, to electrosurgical devices and methods which employ high frequency voltage to cut, ablate or coagulate tissue.

BACKGROUND OF THE INVENTION

Electrosurgical procedures typically rely on the application of very high frequency or radio frequency (RF) electrical power to cut, ablate or coagulate tissue structures. For example, electrosurgery cutting entails heating tissue cells so rapidly that they explode into steam leaving a cavity in the cell matrix. When the electrode is moved and fresh tissue is contacted, new cells explode and the incisions is made. Such electrosurgical cutting involves the sparking of the current to the tissue, also known as the jumping of the RF current across an air gap to the tissue.

Radiofrequency electrodes employed in electrosurgical procedures are generally divided into two categories: monopolar devices and bipolar devices. In monopolar electrosurgical devices, the RF current generally flows from an exposed active electrode through the patient's body, to a passive or return current electrode that is externally attached to a suitable location on the patient's skin. In bipolar electrosurgical devices used in general surgery, both the active and the return electrodes are exposed and are typically in close proximity. The RF current flows from the active electrode to the return electrode through the tissue. Thus, in contrast with the monopolar electrosurgical devices, the return current path for a bipolar device does not pass through the patient.

Electrosurgery which takes place in a conductive fluid environment, such as inside of a joint or body cavity filled with, for instance, normalized saline solution, differs from that described previously in that current is conducted from the active electrode through the fluid to the return electrode. In the case of a monopolar device, the current flows through the patient to the return electrode in the manner previously described. In the case of bipolar devices operating in a conductive fluid environment, the return electrode is not in contact with tissue, but rather is submerged in the conductive fluid in the proximity of the active electrode. Current flow is from the active electrode through the conductive liquid and surrounding tissues to the return electrode of the bipolar device. Whether an electrode is monopolar or bipolar, current flows from all uninsulated surfaces of the active electrode to the return electrode anytime that the electrode is energized. This is in contrast to conventional surgery (also called "open surgery") in which current flows only through electrode surfaces in contact with the patient's tissue.

For an electrode in a fluid environment to vaporize tissue, as in the cutting process described previously, the current density at the electrode/tissue interface must be sufficiently high to cause arcing between the electrode and the patient. If such current density is not achieved, power flows from the active electrode to the return electrode with no desirable clinical effect. In fact, such current flow is highly undesirable since the current flowing from the active electrode heats the conductive fluid in the region surrounding the active electrode. A surgeon using a device which is energized but not arcing to the tissue may believe that he is not affecting tissue in close proximity to the active electrode, however, he may be subjecting the tissue to temperatures approaching 100° C. Even when the electrode is arcing to the tissue, the thermal effects are not limited to vaporization of the tissue. Appreciable undesirable heating of the fluid and tissue in the vicinity to the electrode takes place.

One way of avoiding the negative effects of the undesirable heating of the fluid and adjacent tissue structures is to set the power of the electrosurgical generator to a level that is low enough to minimize the heating of the liquid, but high enough to produce sparks. There is an inherent difficulty, however, in achieving acceptable electrosurgical parameters, since virtually all electrosurgical electrodes are "ignited," i.e., generate sparks, only when brought into contact with tissue, and then, generally, after a time delay of varying lengths. In addition, during electrosurgical procedures, if no sparks are generated, most of the RF power supplied to an electrode operating in a conducting fluid is dissipated in the fluid itself as heat, consequently raising the temperature of the fluid within the joint and the adjacent tissue. If sparks are generated, large fraction of the RF power is used for the creation of sparks in the vicinity of the electrodes, and small fraction heats the surrounding liquid and patient body. Therefore, energizing the electrosurgical electrode without instant initiation of sparks is dangerous and undesirable, as the heating may damage tissue structure uncontrollably in surrounding areas.

Except at very high power levels, monopolar and bipolar electrosurgical electrodes ablators are incapable of generating sparks until they are in contact with tissue, and even then, not instantly. This often substantial delay in spark generation unnecessarily increases the time the probe must be in contact with tissue structure increasing the probability of damage to surrounding tissue structures. During the period when the electrosurgical electrode is energized but before sparking, the heating of the fluid is continuing without any beneficial effect to the patient. This undesirable heating substantially increases the chance of patient burns.

Accordingly, there is a need for an improved electrode for electrosurgical ablation of tissue structures in a conductive fluid which is capable of easy ignition, especially at low power levels. An efficient design for an electrosurgical electrode operating at a low RF power level, as well as methods of fabricating such electrosurgical electrode and methods of utilizing such an electrode in various electrosurgical procedures are also needed.

SUMMARY OF THE INVENTION

In one aspect, the invention provides an electrosurgical electrode capable of achieving instant ignition in a conductive fluid. According to one embodiment, the electrosurgical electrode for instant ignition in a conductive fluid comprises a metallic body portion of various geometries, a metallic tip and a dielectric insulator adjacent the metallic body portion. The metallic tip is recessed from the surface of the dielectric so that the dielectric material and the adjacent recessed metallic tip form a high current density zone for bubble entrapment and instant spark formation. According to another embodiment, lateral walls of the recessed metallic tip form an incidence angle with adjacent dielectric walls, so that the dielectric material and the adjacent recessed angled metallic tip form another high current density zone for bubble entrapment and spark formation. The high current density zones interrupt the conventional flow of fluid and lead to more bubbles sticking to these zones and, thus, to a more efficient creation of steam bubbles. Regardless of whether the metallic tip of the electrode is in contact with a target tissue, spark generation is instantaneous.

In another aspect, the invention provides an apparatus for conducting electrosurgical procedures or interventions comprising at least one electrosurgical probe that includes a shaft having a proximal end and a distal end. The distal end supports at least one electrosurgical electrode for instant ignition in a conductive fluid and comprising a metallic electrode recessed from the surface of the dielectric for about 0.1 to about 5 millimeters. The metallic electrode may have a metallic tip having its lateral walls at an incidence angle with adjacent dielectric walls of about 10 to 80 degrees, more preferably of about 35 to 55 degrees. Alternatively, the metallic tip may comprise a plurality of metallic protuberances of various geometrical forms.

The invention also provides a method of forming an electrosurgical electrode by recessing a metallic electrode from the surface of a dielectric insulator adjacent the metallic electrode for about 0.1 to about 5 millimeters, and forming at least one high current density zone for bubble trap and spark formation. The metallic electrode may be further constructed so that the metallic tip at the proximal part of the metallic electrode has lateral walls at an incidence angle with adjacent dielectric walls of about 10 to 80 degrees, more preferably of about 35 to 55 degrees. Alternatively, the metallic tip may be shaped into a plurality of metallic protuberances with various geometrical forms.

The invention also provides a method of employing an electrosurgical electrode in an electrosurgical procedure for which the total time the electrode needs to be in contact with the tissue structure is decreased. The method comprises the steps of: (i) positioning an electrosurgical electrode adjacent a target tissue, the electrosurgical electrode comprising a metallic electrode recessed from the surface of a dielectric, and then (ii) either submerging the target tissue in an electrical conducting fluid or (iii) directing an electrically conducting fluid to the target tissue to allow the formation of a high current density zone for bubble trap and spark formation in the region formed by the dielectric material and the adjacent recessed portion of the metallic electrode.

These and other features and advantages of the invention will be more apparent from the following detailed description that is provided in connection with the accompanying drawings and illustrated exemplary embodiments of the invention.

DESCRIPTION OF THE PREFERRED EMBODIMENT

The present invention provides an electrosurgical probe with an advanced insulator design and electrosurgical electrode that is capable of achieving instant spark ignition in a conductive fluid, regardless of whether the electrosurgical electrode is in contact or not with a target tissue structure. As described in more detail below, the present invention contemplates the use of a single active electrosurgical electrode or of an array of such active electrosurgical electrodes uniformly distributed over a distal surface of an electrosurgical probe.

Figure 1:
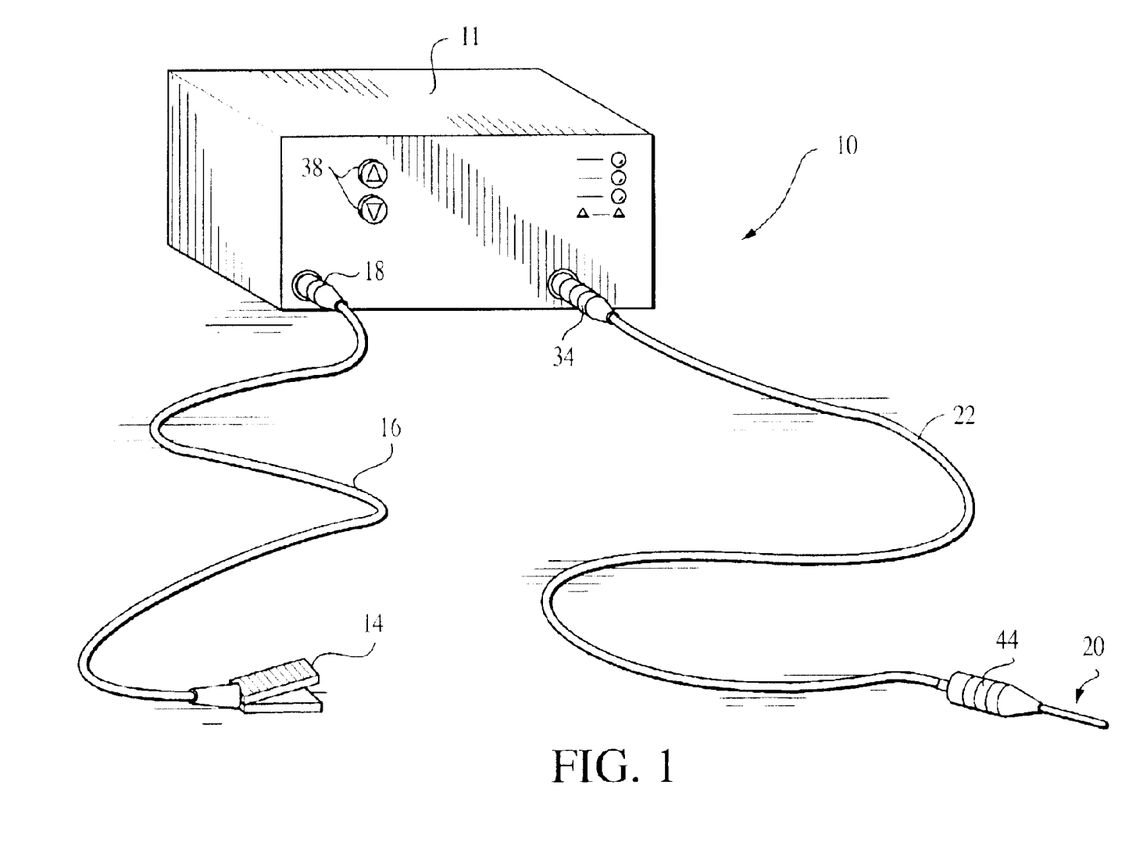
FIG. 1 is a perspective view of an electrosurgical system which includes an electrosurgical probe of the present invention.

Referring now to the drawings, where like elements are designated by like reference numerals, FIG. 1 illustrates a monopolar electrosurgical system 10 that employs a monopolar electrosurgical probe 20 of the present invention. The monopolar electrosurgical system 10 of FIG. 1 may be used, for example, in the treatment of body tissue in minimally invasive procedures within the body, for example, in procedures that require the introduction of a surgical instrument through a percutaneous penetration or through a natural opening in the patient. Although, for simplicity, the invention will be described below with reference to a monopolar electrode, such as the monopolar electrosurgical electrode 100 (FIG. 2), the invention has equal applicability to systems employing bipolar electrosurgical electrodes.

As illustrated in FIG. 1, the monopolar electrosurgical system 10 includes an electrosurgical probe 20 that is connected to receptacle 34 of the electrosurgical power supply 11 by conductor cable 22. The electrosurgical probe 20 comprises a connector housing 44 at its proximal end, and an electrosurgical electrode 100 at its distal end. Power supply 11 provides very high frequency or radio frequency (RF) voltage to the electrosurgical electrode 100. Power supply 11 is also provided with an operator-controllable voltage level adjustment 38 to control the applied voltage level. Thus, a surgeon or a medical operator may manually adjust the voltage level applied to electrosurgical electrode 100 through voltage level adjustment 38.

Power supply 11 of FIG. 1 also includes a foot pedal 14 which may be removably coupled to receptacle 18 through cable connector 16. The foot pedal 14 may be used to place the power supply into a predetermined operation mode, for example, into an "ablation" mode or a "coagulation" mode. In the "ablation" mode, a sufficient voltage is applied to the electrosurgical electrode 100 through voltage level adjustment 38 so that in ablation mode, a voltage is applied to the electrosurgical electrode 100 through voltage level adjustment 38 so that fluid in at least a portion of the active electrode is vaporized and arcing occurs within the bubbles.

The requisite voltage level depends on the characteristics of the electrode and of the RF power supplied to the electrode. Similarly, in the "coagulation" mode, a low enough voltage is applied to the electrosurgical electrode 100 so as to avoid vaporization of the electrically conductive fluid. The foot pedal 14 may also remotely adjust the energy level applied to electrosurgical electrode 100.

Figure 2:
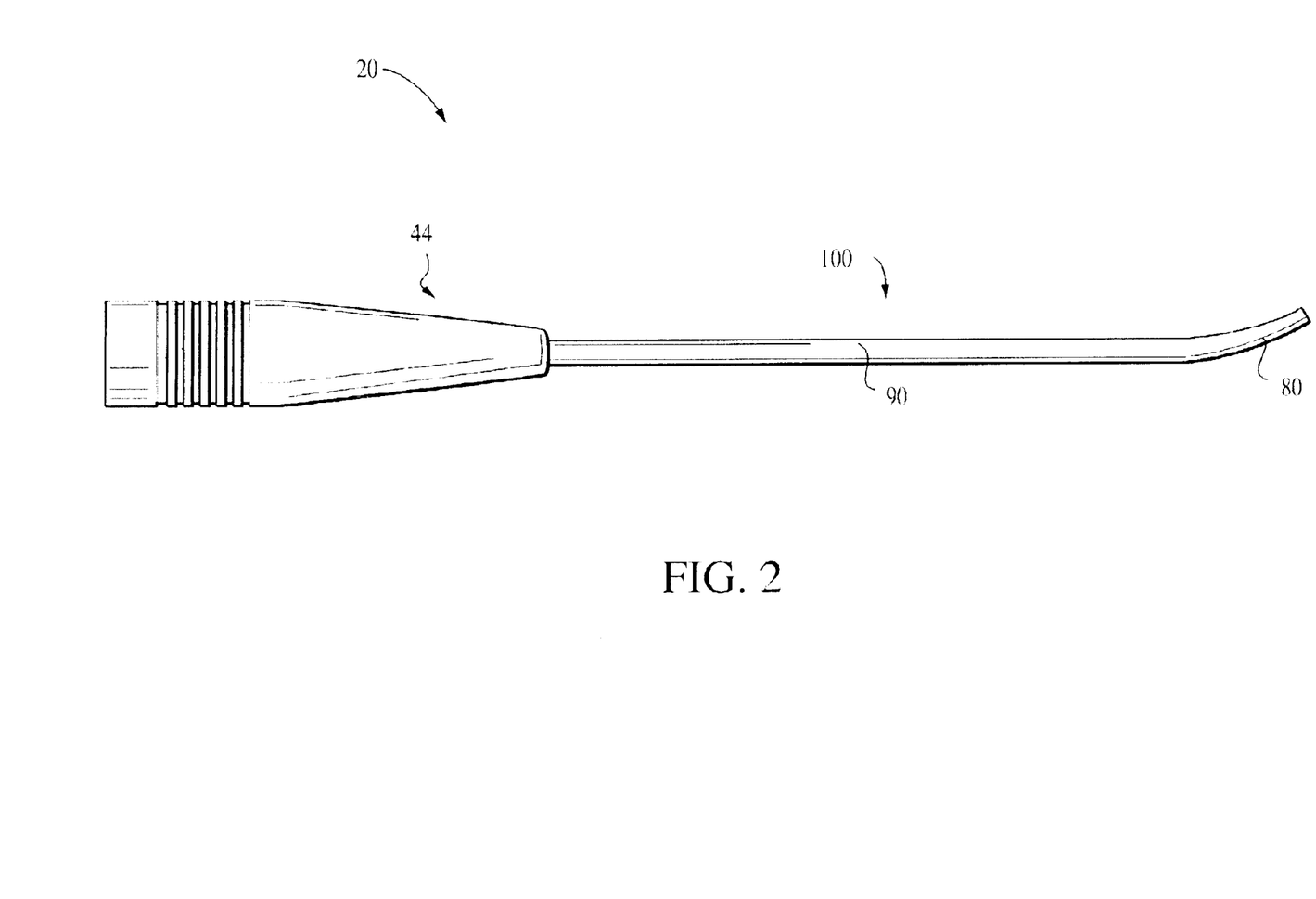
FIG. 2 is a perspective view of the electrosurgical probe of FIG. 1.

The electrosurgical electrode 100 of FIG. 1 is illustrated in more detail in FIG. 2. The electrosurgical electrode 100 comprises an elongated distal shaft 90 having a proximal end adjacent the connector housing 44, and a distal end in contact with or near a distal active electrode 80. The elongated distal shaft 90 may have a variety of configurations for mechanically supporting the distal active electrode 80 and permitting a treating physician to manipulate the distal active electrode 80 from a proximal end of the shaft. As such, the elongated distal shaft 90 may be a tube or a narrow-diameter rod of dimensions that permit the distal active electrode 80 to be introduced through an associated cannula in a minimally invasive procedure, such as arthroscopic or other endoscopic procedures, or into a body cavity, such as the mouth or the abdominal cavity.

The elongated distal shaft 90 may have a length of about at least 10 cm, more preferably of about 10 to about 100 cm, and a diameter of at least 1 mm, more preferably of about 2 to 10 mm. The elongated distal shaft 90 may be flexible or rigid, or may be formed as a combination of a flexible shaft combined with a generally rigid external tube for increased mechanical and physical support. The elongated distal shaft 90 may also include pull wires or shape memory actuators or other known mechanisms for facilitating the positioning of the distal active electrode 80 in the vicinity of the target tissue. In addition, the elongated distal shaft 90 may include other conductive elements and wires that run axially through the shaft and permit connection of the distal active electrode 80 to a connector at the proximal end of the elongated distal shaft 90.

The distal active electrode 80 (FIG. 2) of the electrosurgical electrode 100 of the present invention is illustrated in more detail in FIGS. 3–7. Although, for simplicity, the embodiments of the present invention will be described below with reference to only one distal active electrode 80 as part of the electrosurgical electrode 100, the invention is not limited to this exemplary embodiment. Accordingly, the invention also contemplates the formation of a plurality of such distal active electrode 80 as part of an electrosurgical electrode.

Figure 3:
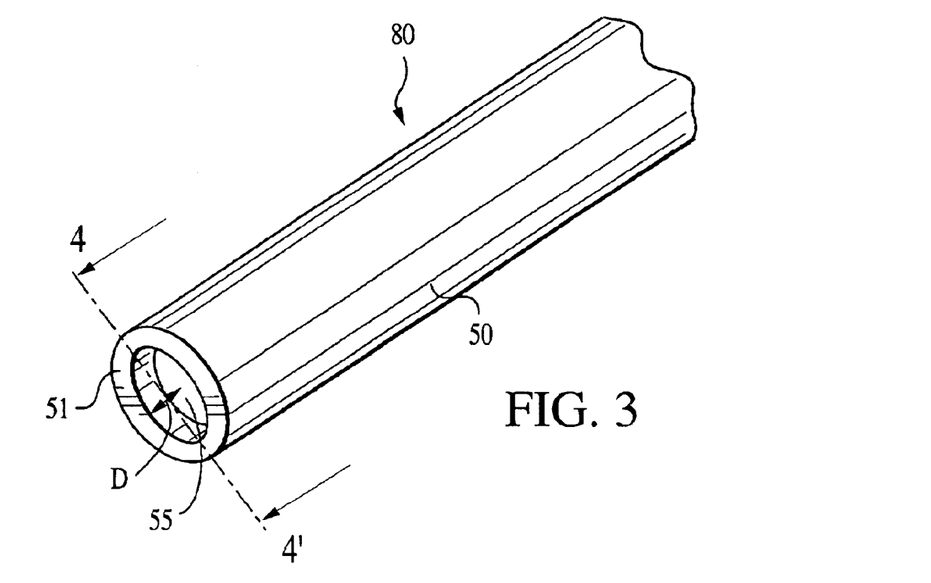
FIG. 3 is schematic three dimensional view of a portion of the electrosurgical probe of FIG. 2.
Figure 4:
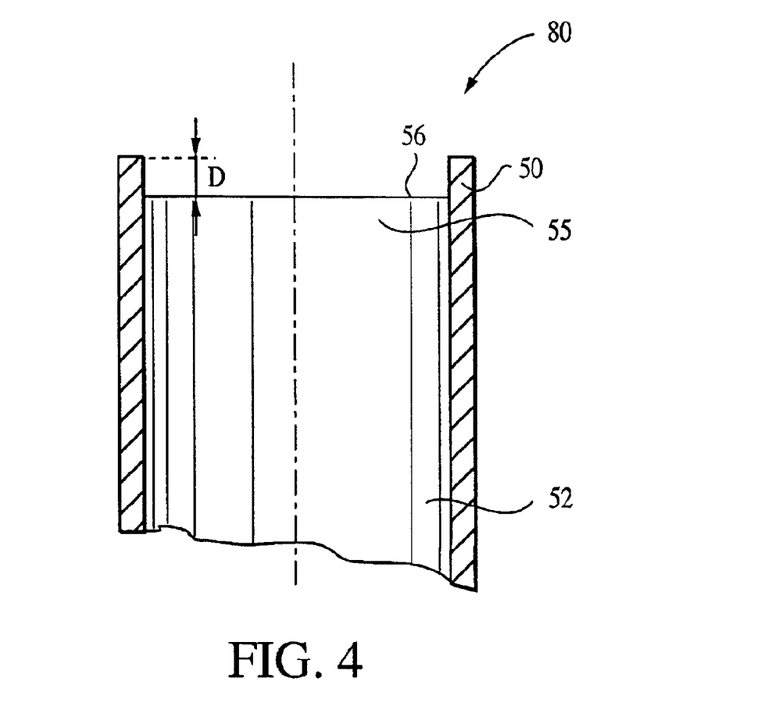
FIG. 4 is an enlarged cross-sectional view of the electrosurgical probe of FIG. 3 taken along line 4—4' and in accordance with a first embodiment of the present invention.

Referring now to FIGS. 3–4, and according to a first embodiment of the present invention, the distal active electrode 80 of the electrosurgical electrode 100 comprises a dielectric material 50, a metallic body region 52 adjacent the dielectric material 50, and a metallic tip 55 located at the distal end of the metallic region 52. As shown in FIGS. 3–4, the metallic tip 55 is recessed by a distance "D" from the tip of the dielectric material 50. The distance D may be about 0.1 to about 5 millimeters, more preferably about 3 millimeters, although distance D is affected by the diameter of metallic tip 55.

The dielectric material 50 may comprise an electrically insulating material such as epoxy, plastic, silicon-based material, ceramic, glass or compositions of these mentioned materials, among many others. The dielectric material 50 may also comprise a perforated shield (not shown) also formed of an electrically insulating material which may be porous and which may include an opening that allows an electrically conductive liquid, for example an isotonic saline solution, to contact the metallic tip 55 and the target tissue. The dielectric material 50 covers and insulates the metallic body region 52 and the metallic tip 55.

The metallic body region 52 and the metallic tip 55 located at the distal end of the metallic region 52 may have various cross-sectional shapes and geometries, for example, cylindrical, rectangular, or elipsoidal, among many others. Thus, although the distal active electrode 80 of the electrosurgical electrode 100 is illustrated in FIG. 3 as having a circular cross-section, the invention is not limited to this embodiment and many other variants may be used, as described above and according to the type of the specific electrosurgical procedure involved.

The metallic body region 52 and the metallic tip 55 located at the distal end of the metallic region 52 may be formed of electrically conductive materials such as metals and metal alloys, for example, stainless steel and stainless steel alloys, platinum and platinum alloys, gold and gold alloys, nickel and nickel alloys, titanium and titanium alloys, and molybdenum and molybdenum alloys, among others. Sufficient clearance exists between the inner surface of dielectric material 50 and outer surface of metallic body region 52 to allow thermal expansion of the metallic body without cracking the dielectric material, particularly at the distal end of these items. The metallic body region 52 may be bonded to the dielectric material 50 by a sealing material (not shown) which is typically an inorganic sealing that provides effective electrical insulation and good adhesion to both the dielectric material 50 and the metallic body region 52. The sealing material may preferably have a compatible thermal expansion coefficient and a melting point above the temperature reached in the region during use.

Figure 5:
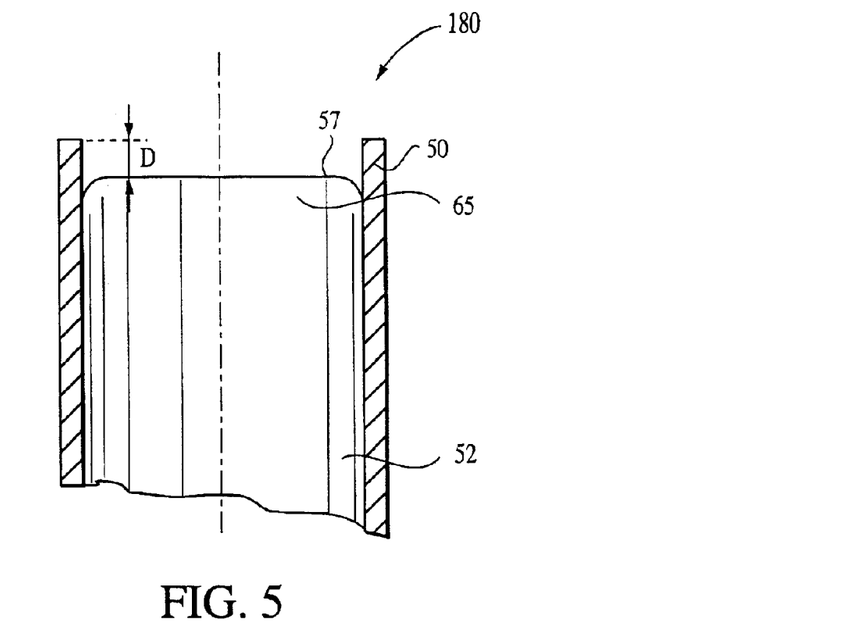
FIG. 5 is an enlarged cross-sectional view of the electrosurgical probe of FIG. 3 taken along line 4—4' and in accordance with a second embodiment of the present invention.

Although contact surface 56 of the metallic tip 55 is illustrated in FIG. 4 as a planar surface, the geometry of this contact surface may vary, primarily according to the location of the target tissue to be treated. Thus, contact surface 56 may be also concave, convex, hemispherical or conical, among many others. FIG. 5, for example, illustrates a second embodiment of the present invention according to which distal active electrode 180 of electrosurgical electrode 100 comprises a metallic body region 52 adjacent a metallic tip 65 having a contact surface 57 which has a convex geometry rather than a planar geometry, as described with reference to the first embodiment. As in the first embodiment, however, the metallic tip 65 is recessed by a distance "D" from the transversal distal dielectric surface 51 (FIG. 3). Again, the distance D may be about 0.5 to about 5 millimeters, more preferably about 3 millimeters.

Figure 6:
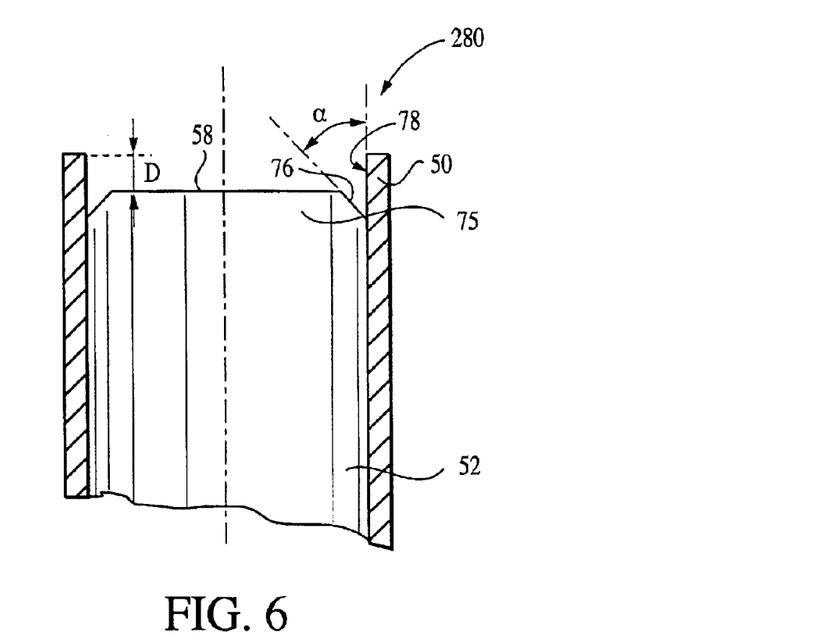
FIG. 6 is an enlarged cross-sectional view of the electrosurgical probe of FIG. 3 taken along line 4—4' and in accordance with a third embodiment of the present invention.

FIG. 6 illustrates a third embodiment of the present invention, according to which distal active electrode 280 of the electrosurgical electrode 100 comprises a metallic body region 52 and a dielectric material 50 adjacent the metallic body region 52. As illustrated in FIG. 6, metallic tip 75 is recessed to a distance "D" from the transversal distal dielectric surface 51 (FIG. 3). Again, the distance D may be about 0.1 to about 5 millimeters, more preferably about 0.3 millimeters.

Metallic tip 75 of the electrosurgical electrode 280 differs, however, from the metallic tip 55 of the first embodiment in that metallic tip 75 of FIG. 6 is shaped so that lateral walls 76 of the metallic tip 75 form an incidence angle "α" (FIG. 6) with adjacent interior dielectric walls 78. This way, lateral walls 76 of the metallic tip 65 and dielectric walls 78 form angle α of about 10 to 80 degrees, more preferably of about 35 to 55 degrees.

Figure 7:
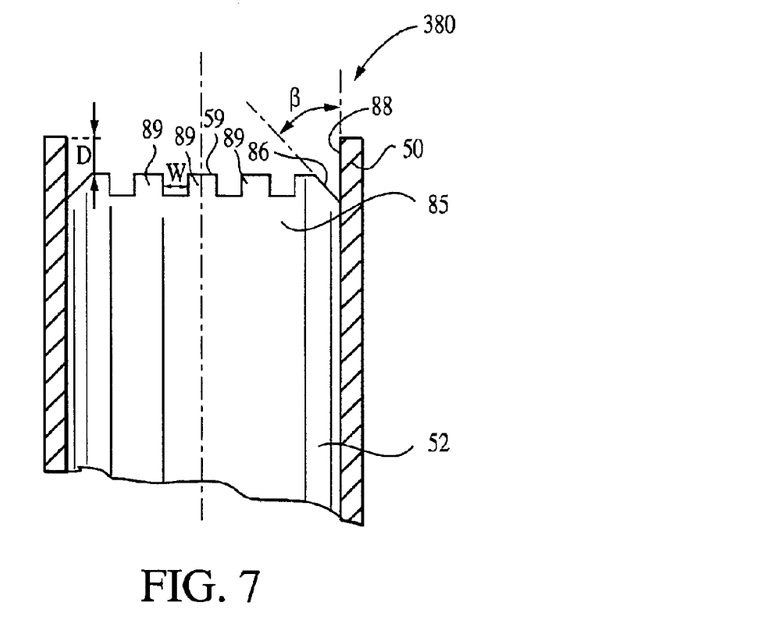
FIG. 7 is an enlarged cross-sectional view of the electrosurgical probe of FIG. 3 taken along line 4—4' and in accordance with a fourth embodiment of the present invention.

FIG. 7 illustrates yet another embodiment of the present invention. Metallic tip 85 of distal active electrode 380 (FIG.

7) of the electrosurgical electrode 100 is recessed by a distance "D" from the transversal distal dielectric surface 51 (FIG. 3) of the dielectric material 50. As in the previous embodiments, the distance D may be about 0.1 to about 5 millimeters, more preferably about 0.3 millimeters. Metallic tip 85 of FIG. 7 is shaped so that lateral walls 86 of the metallic tip 85 form an incidence angle "β" (FIG. 7) with adjacent interior dielectric walls 88. This way, lateral walls 86 of the metallic tip 85 and dielectric walls 88 form angle β of about 10 to 80 degrees, more preferably of about 35 to 55 degrees. As also illustrated in FIG. 7, contact surface 59 of the metallic tip 85 is shaped into a plurality of protuberances or "teeth" 89 having various geometrical shapes and spaced apart at a distance "w" (FIG. 7) of about 0.1 to about 2 millimeters, more preferably 0.25 millimeters. For example, protuberances 89 of FIG. 7 are illustrated as having a rectangular shape with dimensions of about 0.25 to 1 millimeters, but many other geometries are possible, for example, trapezoidal shape, among others.

The electrosurgical electrode of the present invention described above with reference to FIGS. 1–7 may be employed in various electrosurgical procedures for which the total time the electrode needs to be in contact with the tissue structure is substantially decreased. As such, the electrosurgical electrode 100 (FIGS. 1–7) of the present invention which is capable of instant spark ignition may be employed in a variety of surgical medical procedures in the presence of an electrically conductive fluid to remove and/or modify a particular target tissue. Accordingly, the electrosurgical electrode 100 of the present invention may be used in a conventional open surgery environment or in other, less invasive, techniques that use cannulas or various port access devices if conductive fluid is present. The present invention has also applications in surgical procedures where the target tissue is flooded with, or submerged in, an electrically conductive fluid such as in many arthroscopic procedures for ablation, coagulation, shaping and cutting of various body parts such as the knee, shoulder, hip, ankle, elbow, hand or foot.

The present invention has also equal applicability to surgical procedures where the target tissue is flooded with a natural conductive fluid of the human body, such as blood or lymphatic plasma, for example, which act as electrically conductive fluids. Nevertheless, an electrically conductive fluid introduced into the patient's body is preferred over blood because blood tends to coagulate at certain temperatures. In addition, the patient's blood or plasma may lack the necessary conductivity to adequately carry out the particular electrosurgical procedure desired.

Surgical procedures using the electrosurgical electrode 100 of the invention include introducing the electrode assembly in close proximity to the surgical site through an artificial conduit or a cannula, or through a natural conduit which may be in an anatomical body cavity or space or one created surgically. For the purposes of the present invention, the terms "close proximity" and "proximity" are defined as "in contact with" or "at a distance of about 0.1 to about 10 millimeters." The cavity or space may be distended during the procedure using a fluid or may be naturally held open by anatomical structures. In addition, the surgical site may be bathed in a continuous flow of conductive fluid, such as saline solution, to fill and distend the cavity. The procedures may include simultaneous viewing of the site via an endoscope or using an indirect visualization means.

Figure 8:
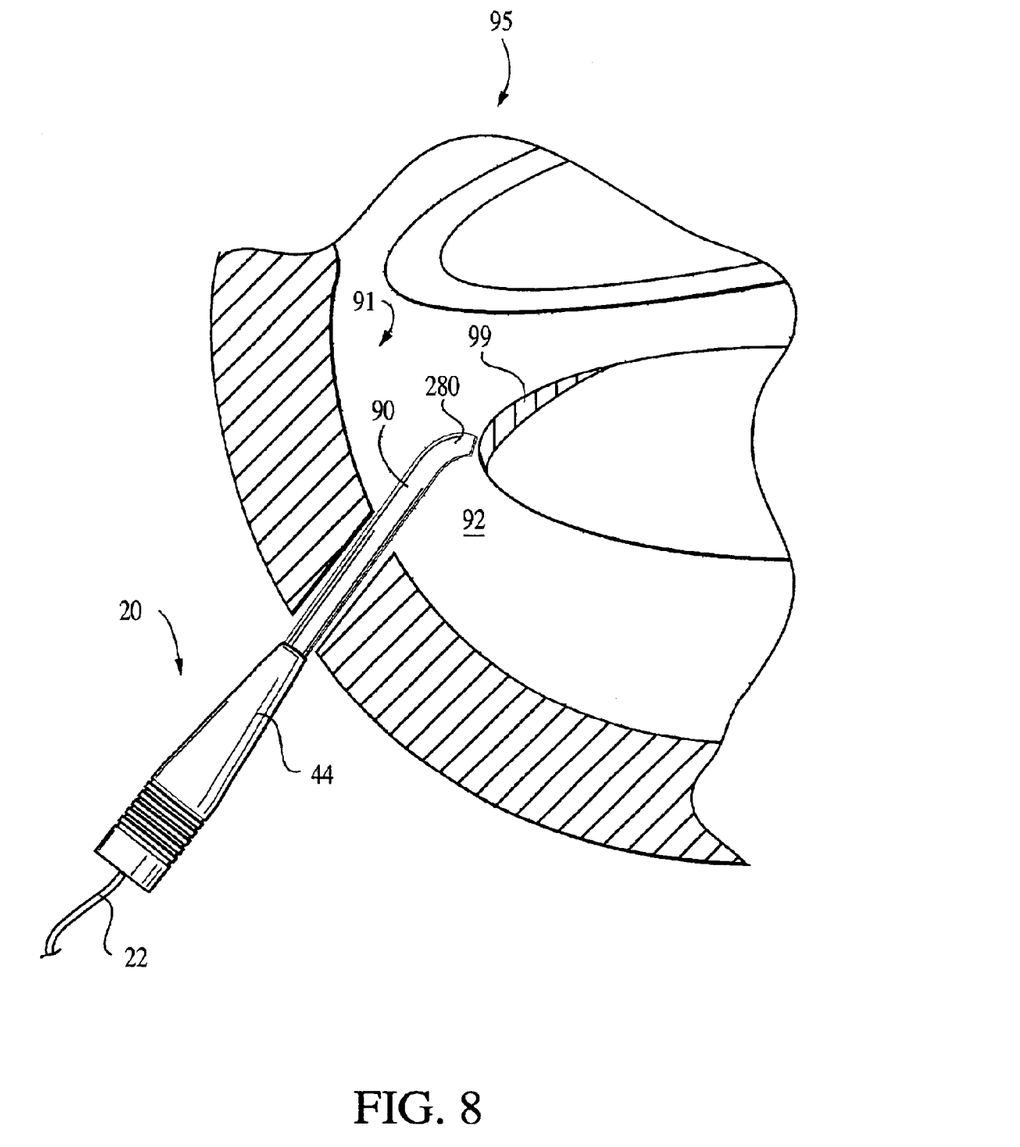
FIG. 8 is a schematic cross-sectional view of a knee joint undergoing an electrosurgical procedure employing an electrosurgical electrode of the present invention.

To better illustrate an exemplary surgical procedure conducted with the electrosurgical electrode 100 of the present invention, reference is now made to FIG. 8, which illustrates a schematic cross-sectional view of a knee joint region 95. The knee joint region 95 of FIG. 8 may undergo an arthroscopic procedure, for example, with electrosurgical probe 20 having electrosurgical electrode 100 and distal active electrode 280 (FIG. 6) fabricated according to the third embodiment of the present invention. As known in the art, an endoscope (not shown) may be provided at one end with the distal active electrode 280, and then introduced into knee cavity 92 (FIG. 8) containing electrically conductive fluid 91 (FIG. 8) and in close proximity to target tissue 99 (FIG. 8). If the target tissue 99 of the knee joint region 95 is a damaged meniscus, for example, then target tissue 99 may undergo a partial or complete electrosurgical meniscectomy using active electrode 280. Alternatively, the endoscope may be introduced separately from the electrosurgical electrode 280, via separate access means in a surgical technique commonly known as triangulation. In any event, knee cavity 92 may be distended during the arthroscopic procedure using electrically conductive fluid 91, so that target tissue 99 may be bathed in a continuous flow of conductive fluid 91, which may be preferably a saline solution.

Once distal active electrode 280 is positioned in the proximity of the target tissue 99 and the target tissue 99 is submerged in the electrically conductive fluid 91, the electrosurgical probe 20 is energized by the electrosurgery power supply 11 (FIG. 1). The power supply delivers radio frequency energy, typically in the range of 100 kHz to 3 MHz, through the cable system 22 (FIGS. 1 and 8) to the electrosurgical electrode 100 and further to the distal active electrode 280.

Figure 9:
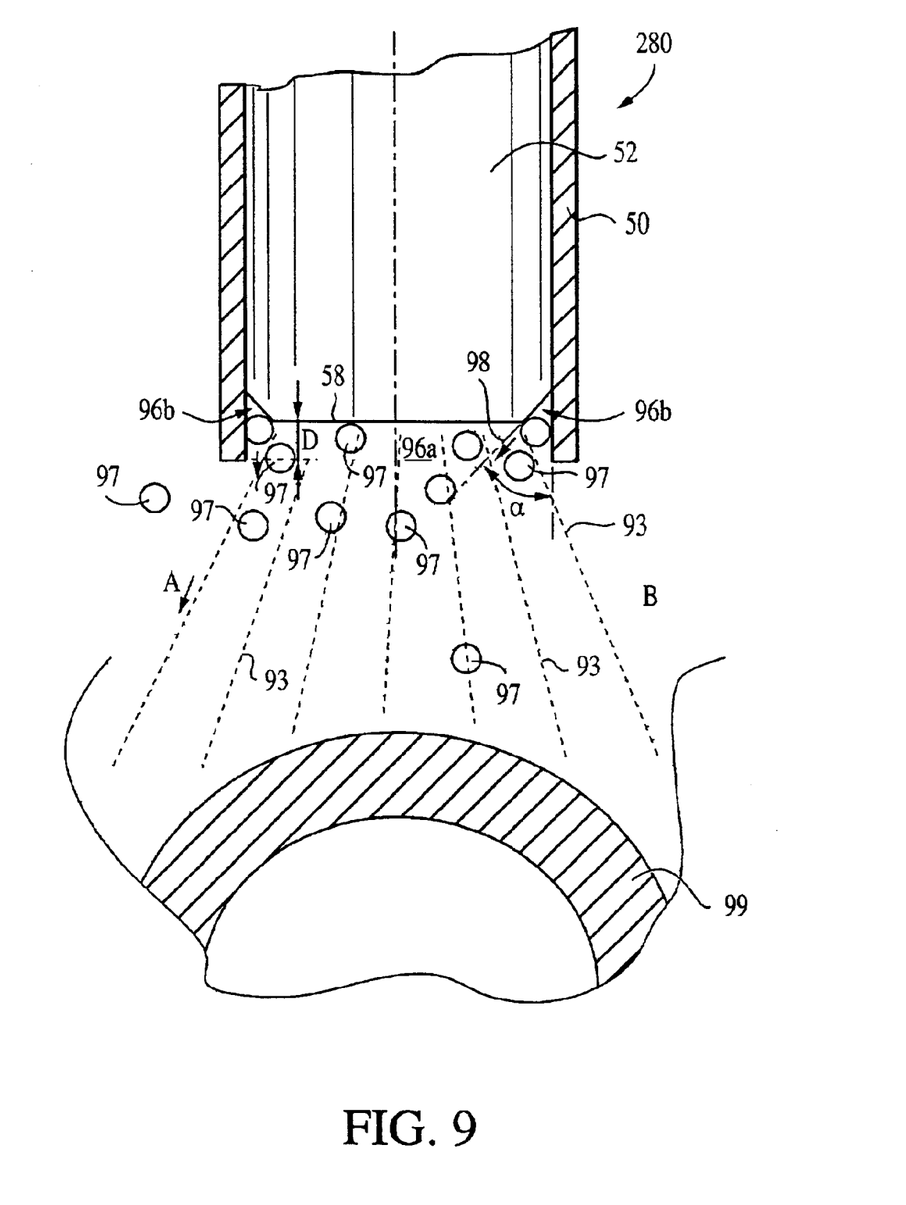
FIG. 9 is an enlarged cross-sectional view of the electrosurgical electrode of the third embodiment of the present invention in proximity to a target tissue of the structure of FIG. 8.

For a better understanding of the electrical and conduction phenomenas that occur when the distal active electrode 280 is energized by power supply 11, reference is made to FIG. 9, which is an enlarged cross-sectional view of the distal active electrode 280 in the proximity of the target tissue 99 of the knee joint region 95. The high radio frequency energy is dissipated in the electrically conductive fluid 91 and is directed toward the target tissue 99, forming therefore high density electrical flux lines 93, illustrated in FIG. 9. As a result of the dissipation of the high radio frequency energy in the electrically conductive fluid 91, the conductive fluid 91 is heated from an initial temperature $T_i$ (typically the body temperature) to a final temperature $T_f$ in the range of about 39 to about 50° C.

As a result of the metallic tip 75 being recessed to distance D from the distal transversal dielectric surface 51, a first high current density zone or first pocket 96a (FIG. 9) is formed in the region delineated by the contact surface 58 of the metallic tip 75 and the protruding portions of the dielectric layer 50. Similarly, as a result of the lateral walls 76 (FIG. 6) of the metallic tip 75 forming angle α (FIG. 6) with adjacent dielectric walls 78, second high current density zones or second pockets 96b (FIG. 9) are formed in the regions delineated by the lateral walls 76 of the metallic tip 75 and adjacent dielectric walls 78.

These high current density zones 96a, 96b create traps for conductive fluid 91 which is heated to the final temperature $T_f$. Steam bubbles 97 (FIG. 9), which are created near the dielectric material 50 as well near the contact surface 58 of the metallic tip 75 as a result of heating of the conductive fluid 91, are also trapped in the high current density zones 96a, 96b and eventually form sparks 98 (FIG. 9). Bubbles 97 that are created and trapped in these high current density zones or pockets 96a, 96b further interfere with high density flux lines 93 and interrupt, therefore, the conventional flow of flux lines 93 (illustrated as arrow A in FIG. 9). When steam bubbles 97 reach a critical size, the electrical resistance to current flow is less through bubbles 97 than through the conductive fluid 91 and sparking occurs within bubbles 97. In this manner, even if the distal active electrode 280 is not in physical contact with the target tissue 99, arcing within bubbles 97 is virtually instantaneous in the high current density zones 96a, 96b and is generated independent of the position of the electrosurgical electrode relative to the target tissue 99 to be treated.

The present invention provides, therefore, a method for efficiently generating sparks independent of the position of an electrosurgical electrode relative to a target tissue, and even when the electrode is not in contact with the target tissue. Sparks 98 generated by bubbles 97 in the high density zones or pockets 96a, 96b when the electrosurgical probe 20 is immersed in conductive fluid 91 and away from target tissue 99 do not lead to additional undesirable tissue heating in the knee joint region 95 (FIG. 8) because the current density is distributed mainly in the high density zones or pockets 96a, 96b of the present invention. In addition, the power needed for operation is smaller in comparison with traditional probes and the total current decreases while sparks are generated, thereby reducing the risk of patient burns. Accordingly, the present invention eliminates the ignition problems of conventional electrosurgical probes, makes operation of such electrosurgical probes more controllable, and decreases the total time that the electrosurgical probe needs to be in contact with a particular tissue structure.

Although the present invention has been described above with reference to arthroscopic surgery of a knee joint structure, the invention is not limited to the above embodiments. Accordingly, the electrosurgical electrode 100 (FIGS. 1–7) of the invention may be employed for a variety of arthroscopic procedures, for example, in the dissection, resection, vaporization, desiccation and coagulation of tissue structures in various endoscopic and percutaneous procedures performed on joints of the body including, but not limited to, spinal and other non-synovial joint techniques. Arthroscopic procedures encompassed by the present invention may further include: lateral retinacular release of the knee joint; removal of anterior and posterior cruciate ligaments; labral tear resection; acromioplasty, bursectomy and subacromial decompression of the shoulder joint; anterior release of the tempomandibular joint; synovectomy, cartilage debridement, chondroplasty, division of intra-articular adhesions, fracture and tendon debridement as applied to any of the synovial joints of the body; inducing thermal shrinkage of joint capsules as a treatment for recurrent dislocation, subluxation or repetitive stress injury to any articulated joint of the body; discectomy either in the treatment of disc prolapse or as part of a spinal fusion via a posterior or anterior approach to the cervical, thoracic and lumbar spine or any other fibrous joint for similar purposes; excision of diseased tissue and haemostasis, among others.

The electrosurgical electrode 100 (FIGS. 1–7) of the present invention may be also used in hysteroscopic surgical procedures or urological endoscopic (urethroscopy, cystoscopy, ureteroscopy and nephroscopy) and percutaneous interventions. Hysteroscopic procedures may include: removal of submucosal fibroids, polyps and malignant neoplasms; resection of congenital uterine anomalies such as a septum or subseptum; division of synechiae (adhesiolysis); ablation of diseased or hypertrophic endometrial tissue; and haemostasis. Urological procedures may include: electro-vaporization of the prostate gland (EVAP) and other similar procedures commonly referred to as transurethral resection of the prostate (TURP) including, but not limited to, interstitial ablation of the prostate gland by a percutaneous or perurethral route whether performed for benign or malignant disease; transurethaal or percutaneous resection of urinary tract tumors; division of strictures as they may arise at the pelviureteric junction (PUJ), ureter, ureteral orifice, bladder neck or urethra; correction of ureterocoele, among others.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. An electrosurgical probe comprising:
a shaft having a proximal end and a distal end, and at least one active electrode located at or near said distal end, said at least one active electrode comprising a metallic body region terminating in a non-hollow metallic tip, said non-hollow metallic tip being surrounded by a dielectric material and fixedly attached to said dielectric material,
wherein a longitudinal portion of said metallic body of said active electrode has a cross-section having a perimeter that contacts said dielectric material at every point, said metallic tip being recessed from a distal transversal surface of said dielectric material.

2. The electrosurgical probe of claim 1, wherein said metallic tip is recessed for about 0.1 to about 5 millimeters.

3. The electrosurgical probe of claim 1, wherein lateral walls of said metallic tip form an incidence angle with adjacent lateral walls of said dielectric material.

4. The electrosurgical probe of claim 3, wherein said incidence angle is of about 10 to 80 degrees.

5. The electrosurgical probe of claim 4, wherein said incidence angle is of about 35 to 55 degrees.

6. The electrosurgical probe of claim 1, wherein said metallic tip has a planar distal surface.

7. The electrosurgical probe of claim 1, wherein said metallic tip has a convex distal surface.

8. The electrosurgical probe of claim 1, wherein said metallic tip further comprises a plurality of rectangular protuberances.

9. An electrosurgical system for the electrosurgical treatment of tissue immersed in a conductive fluid comprising a power supply source; and
means for applying high frequency voltage to an electrosurgical probe, said electrosurgical probe comprising a shaft having a proximal and a distal end; and an active electrode located at or near said distal end,
said active electrode comprising a metallic body region terminating in a non-hollow metallic tip, said non-hollow metallic tip being surrounded by a dielectric material,
wherein a longitudinal portion of said metallic body of said active electrode has a cross-section having a perimeter that contacts said dielectric material at every point, said metallic tip being recessed by about 0.1 to about 5 millimeters from a distal tip of said dielectric material.

10. The electrosurgical system of claim 9, wherein lateral walls of said metallic tip form an incidence angle of about 10 to 80 degrees with adjacent lateral walls of said dielectric material.

11. The electrosurgical system of claim 10, wherein said incidence angle is of about 35 to 55 degrees.

12. The electrosurgical system of claim 9, wherein said metallic tip further comprises a plurality of rectangular protuberances.

13. A method of conducting an electrosurgical procedure comprising the steps of providing an active electrode of an electrosurgical probe, said active electrode comprising a metallic body region terminating in a non-hollow metallic tip, said non-hollow metallic tip being surrounded by a dielectric material, wherein a longitudinal portion of said metallic body of said active electrode has a cross-section having a perimeter that contacts said dielectric material at every point, said metallic tip being recessed from a distal tip of said dielectric material; positioning said active electrode in the proximity of a tissue to be treated in the presence of an electrically conductive fluid; applying a high frequency voltage to said active electrode to generate an electric field adjacent said recessed metallic tip; and effecting ablation of at least a portion of said tissue to be treated.

14. The method of claim 13, wherein said metallic tip is recessed from said distal tip by about 0.1 to about 5 millimeters.

15. The method of claim 13, wherein lateral walls of said metallic tip further form an incidence angle with adjacent lateral walls of said dielectric material.

16. The method of claim 15, wherein said step of applying said high frequency voltage to said active electrode further comprises generating an electric field adjacent said incidence angle.

17. The method of claim 15, wherein said incidence angle is of about 10 to 80 degrees.

18. The method of claim 17, wherein said incidence angle is of about 35 to 55 degrees.

19. The method of claim 17, wherein said metallic tip is further formed with a plurality of protuberances, each of said plurality of protuberances being spaced from each other by about 0.5 to about 2 millimeters.

20. A method of providing instant spark formation for use in an electrosurgical procedure, said method comprising:
providing an active electrode of art electrosurgical probe, said active electrode comprising a metallic body region terminating in a non-hollow metallic tip, said non-hollow metallic tip being surrounded by a dielectric material, wherein a longitudinal portion of said metallic body of said active electrode has a cross-section having a perimeter that contacts said dielectric material at every point, said metallic tip being recessed by about 0.1 to about 5 millimeters from a distal transversal surface of said dielectric material, and wherein lateral walls of said metallic tip are further forming an incidence angle of about 10 to about 80 degrees with lateral walls of said dielectric material; positioning said active electrode in the proximity of a tissue to be treated in the presence of an electrically conductive fluid; and applying a high frequency voltage to said active electrode to generate an electric field adjacent said recessed metallic tip and said incidence angle.

* * * * *